United States Patent
Konrath et al.

(10) Patent No.: US 8,455,212 B2
(45) Date of Patent: Jun. 4, 2013

(54) ASSAYS FOR HUMAN NT-PRO B-TYPE NATRIURETIC PEPTIDE, HUMAN PRO B-TYPE NATRIURETIC PEPTIDE AND HUMAN B-TYPE NATRIURETIC PEPTIDE

(75) Inventors: John George Konrath, Lake Villa, IL (US); Jeffrey Allen Moore, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 523 days.

(21) Appl. No.: 12/623,405

(22) Filed: Nov. 21, 2009

(65) Prior Publication Data
US 2011/0124012 A1 May 26, 2011

(51) Int. Cl.
G01N 33/543 (2006.01)
G01N 33/53 (2006.01)
G01N 33/68 (2006.01)
C07K 16/26 (2006.01)

(52) U.S. Cl.
USPC .......................... 435/7.94; 436/518; 436/86

(58) Field of Classification Search
None
See application file for complete search history.

(56) References Cited

U.S. PATENT DOCUMENTS

| | | | |
|---|---|---|---|
| 5,006,309 | A | 4/1991 | Khalil et al. |
| 5,063,081 | A | 11/1991 | Cozzette et al. |
| 5,089,424 | A | 2/1992 | Khalil et al. |
| 6,162,902 | A | 12/2000 | Mischak et al. |
| 2003/0170881 | A1 | 9/2003 | Davis et al. |
| 2004/0018577 | A1 | 1/2004 | Emerson Campbell et al. |
| 2005/0054078 | A1 | 3/2005 | Miller et al. |
| 2006/0160164 | A1 | 7/2006 | Miller et al. |

FOREIGN PATENT DOCUMENTS

| | | |
|---|---|---|
| WO | WO 2007/041645 A2 * | 4/2007 |
| WO | WO 2007/110779 A2 * | 10/2007 |
| WO | WO2009066010 A1 | 5/2009 |

OTHER PUBLICATIONS

Cataliotti, A. et al. "Circulating Natriuretic Peptide Concentrations in Patients With End-Stage Renal Disease: Role of Brain Natriuretic Peptide as a Biomarker for Ventricular Remodeling" Mayo Clin Proc. 2001;76:1111-1119.*
HyTest Ltd, DataSheet for Catalogue # 4NT1; Product Name "Monoclonal mouse anti-human N-terminal proBNP (NT-proBNP)", retrieved from http://www.hytest.fi/sites/hytest.fi/files/4NT1_DS.pdf on Sep. 11, 2012 (one page).*
HyTest News, ProBNP and ProBNP Derived Peptides BNP and NT-ProBNP, 2007, Internet citation (Jun. 2007), XP002589188.
International Search Report for Application No. PCT/US2010/056932, mailed on Feb. 1, 2011, 6 pages.
Seferian K.R., et al., "The Brain Natriuretic peptide (BNP) Precursor Is the Major Immunoreactive Form of BNP in Patients with Heart Failure," Clinical Chemistry, 2007, vol. 53 (5), pp. 866-873.
Written Opinion for Application No. PCT/US2010/056932, mailed on Feb. 1, 2011, 6 pages.
Cataliotti et al., "Circulating Natriuretic Peptide concentrations in patients With End-Stage Renal Disease: Role of Brain Natriuretic Peptide as a Biomarker for Ventricular Remodeling," Mayo Clinic Proc, 2001, pp. 1111-1119, vol. 76 (11).
Hammerer Lercher, et al., "Analysis of Circulating Forms of proBNP and NT-proBNP in Patients with Severe Heart Failure", Clinical Chemistry, 2008, 54(5), 858-865.
Haugland, et al., "Handbook of Fluorescent Probes and Research Chemicals, Book cover and table of contents, Molecular Probes", 1996, ix-xii, (five pages total).
Hunt et al., "The Amino-Terminal Portion of Pro-Brain Natriuretic Peptide (Pro-BNP) Circulates in Human Plasma," Biochemical and Biophysical Research Communications, 1995, pp. 1175-1183, vol. 214 (3).
Liang, et al., "Evidence for Functional heterogeneity of Circulating B-Type Natriuretic Peptide", Journal of the American College of Cardiology, 2007, 49(10), 1071-1078.
Polak et al., Introduction to Immunocytochemistry, 1997, Ed. 2, Springer Verlag, pp. v-ix.
Schellenberger, et al., "The precursor to B-type natriuretic peptide is an 0-linked glycoprotein", Archives of Biochemistry and Biophysics, 2006, 451, 160-166.
Seferian., et al., "Immunodetection of Glycosylated NT-proBNP Circulating in Human Blood," Clinical Chemistry, 2008, 54(5), 866-873.
Tateyama et al., "Concentrations and Molecular Forms of Human Brain Natriuretic Peptide in Plasma," Biochemical and Biophysical Research Communications, 1992, pp. 760-767, vol. 185 (2).
Yandle T.G., "Minisymposium: The Natriuretic Peptide Hormones; Biochemistry of natriuretic peptides", Journal of Internal Medicine, Journal of Internal Medicine, 1994, 235, 561-576.

* cited by examiner

*Primary Examiner* — Christine Foster
(74) *Attorney, Agent, or Firm* — Cheryl L. Becker

(57) ABSTRACT

The present disclosure relates to assays for detecting and/or quantifying the amount of human NT-pro B-type natriuretic peptide, human pro B-type natriuretic peptide and human B-type natriuretic peptide in a test sample.

8 Claims, 3 Drawing Sheets

FIGURE 1
FIGURE 1A
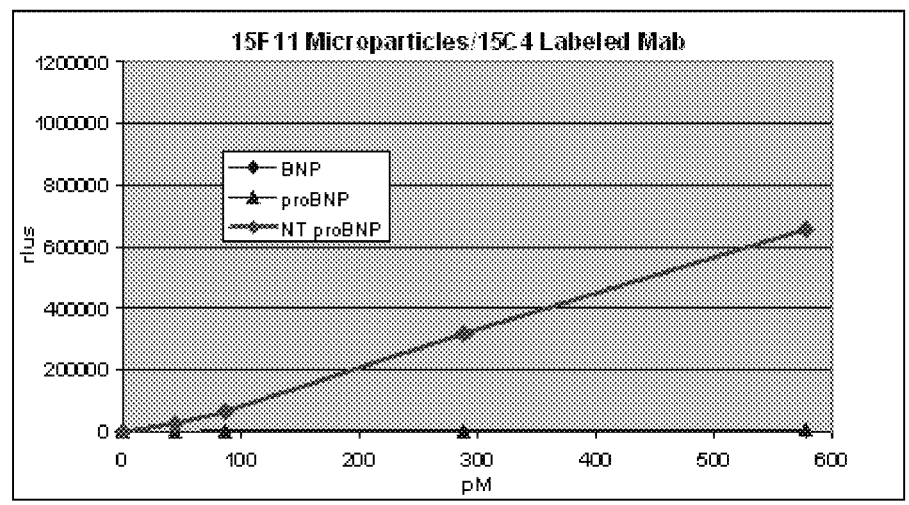
FIGURE 1B
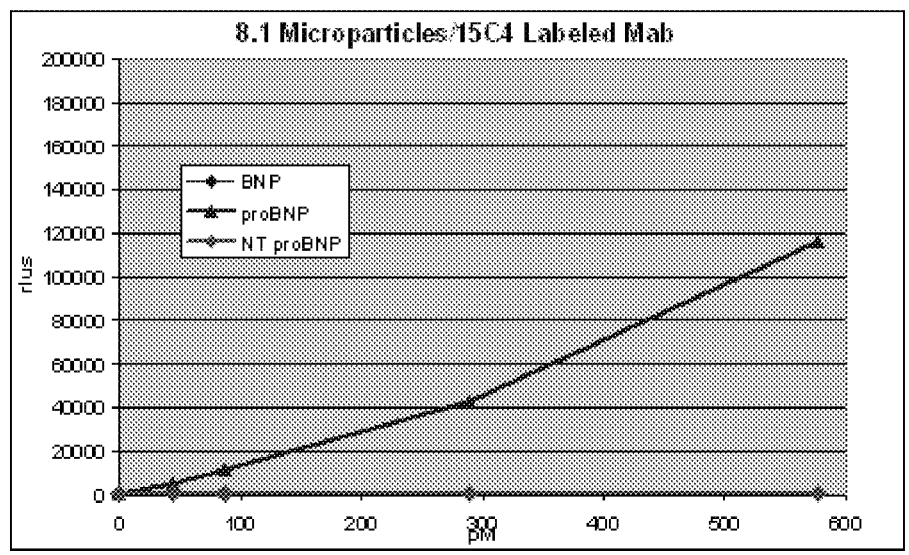

FIGURE 2
Figure 2A
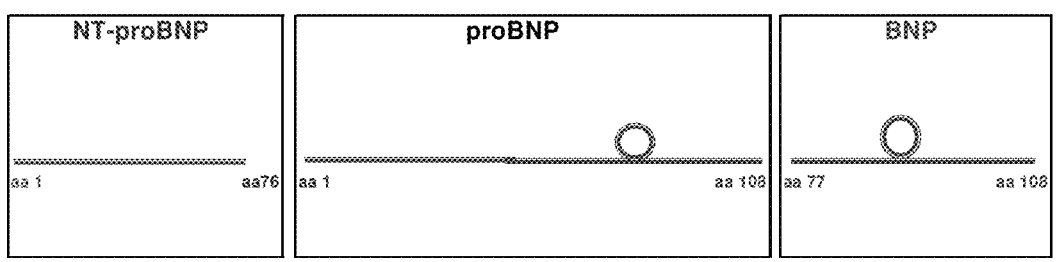
Figure 2B
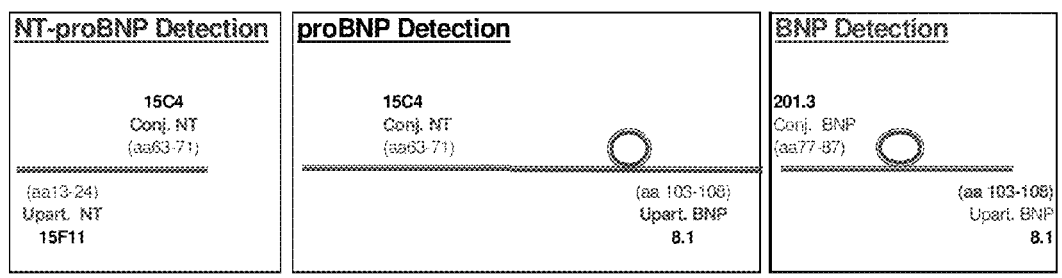

ASSAYS FOR HUMAN NT-PRO B-TYPE NATRIURETIC PEPTIDE, HUMAN PRO B-TYPE NATRIURETIC PEPTIDE AND HUMAN B-TYPE NATRIURETIC PEPTIDE

RELATED APPLICATION INFORMATION

None.

TECHNICAL FIELD

In one aspect, the present disclosure relates to assays for detecting and/or quantifying the amount of human NT-pro B-type natriuretic peptide, human pro B-type natriuretic peptide and human B-type natriuretic peptide in aliquots obtained from a test sample. In another aspect, the present disclosure relates to immunodiagnostic reagents for use in an assay for detecting and/or quantifying the amount of human NT-pro B-type natriuretic peptide, human pro B-type natriuretic peptide and human B-type natriuretic peptide in a test sample. In still yet another aspect, the present disclosure relates to kits for use in performing an assay for detecting and/or quantifying the amount of human NT-pro B-type natriuretic peptide, human pro B-type natriuretic peptide and human B-type natriuretic peptide in a test sample.

BACKGROUND

Atrial natriuretic peptide (hereinafter "ANP"), B-type natriuretic peptide (hereinafter "BNP"), C-type natriuretic peptide (hereinafter "CNP") and Dendroaspis natriuretic peptide (hereinafter "DNP") are each members of a family of hormones known as "natriuretic peptides". ANP and BNP share a wide spectrum of biological properties and belong to the cardiac natriuretic system. Both ANP and BNP are of myocardial cell origin while CNP is of endothelial cell origin. DNP was isolated from the venom of the green mamba snake and possesses structural similarity to ANP, BNP and CNP.

ANP is secreted by the heart in the atria. ANP has a 17 amino acid ring closed by a disulfide bond between two cysteine residues. Eleven of the seventeen amino acids in the ring are conserved across ANP, BNP, CNP and DNP. In addition to the 17 amino acid ring structure, ANP has an amino-terminal tail of 6 amino acids and a carboxy-terminal tail of 5 amino acids. ANP is produced as a 126 amino acid pro-ANP form that is the major storage form of ANP. After proteolytic cleavage between amino acids 98 and 99, the mature 28 amino acid peptide ANP is found in coronary sinus plasma (See Yandle, *J. Internal Med.*, 235:561-576 (1994)).

BNP received its name because it was first isolated from porcine brain, thus, initially, "BNP" stood for "brain natriuretic peptide". However, because BNP was found to belong to the cardiac natriuretic system, the word "brain" was changed to "B-type". Therefore, "BNP" now refers to "B-type natriuretic peptide". In humans, BNP is secreted by the heart through the coronary sinus, predominantly from the cardiac ventricles. The pre-pro peptide precursor of human BNP (hereinafter "human pre-proBNP") is 134 amino acids in length (SEQ ID NO:1) and comprises a short signal peptide, which is enzymatically cleaved off to release the human pro peptide of BNP (hereinafter "human proBNP") which is 108 amino acids in length (SEQ ID NO:2). Human proBNP is further cleaved into an N-terminal pro peptide of human BNP (hereinafter "human NT-proBNP") which is 76 amino acids in length (SEQ ID NO:3) and the active hormone, human BNP (hereinafter "hBNP" or "hBNP-32"), which is 32 amino acids in length (SEQ ID NO:4). It has been suggested that each of human NT pro-BNP, hBNP-32, and human proBNP-can circulate in human plasma (See, Tateyama et al., *Biochem. Biophys. Res. Commun.* 185: 760-7 (1992); Hunt et al., *Biochem. Biophys. Res. Commun.* 214: 1175-83 (1995)).

CNP was first found in the brain, however, most of it originates in endothelial and renal cells. It is widely distributed in the vasculature, brain, bone and endothelium. Little if any CNP is present in the heart. Pro-CNP is a 103 amino acid peptide that is processed into either CNP-53 (amino acids 51 to 103) or CNP-22 (amino acids 82 to 103) that are the active peptides. Like ANP, CNP has a 17 amino acid ring closed by a disulfide bond between cysteine residues. In addition to this 17 amino acid ring structure, CNP-22 has an amino-terminal tail of 5 amino acids and contains no carboxy-terminal tail. CNP-53 is identical to CNP-22 except for a 31 amino acid extension at the amino terminal end.

As mentioned previously, DNP was isolated from the venom of the green mamba snake. The mature form of DNP is made up of 38 amino acids. DNP-like immunoreactivity (DNP-LI) has been reported in human plasma and the plasma concentration of DNP-LI has been found to be elevated in patients with congestive heart failure (See, Cataliotti, et al., *Mayo Clin. Proc.*, 76:111-1119 (2001)). Additionally, it is also known that the infusion of synthetic DNP results in marked natriuresis and diuresis in association with increased plasma and urinary cyclic guanosine monophosphate. Id.

In humans, heart disease can stimulate the secretion of ANP and BNP. In fact, the secretion of ANP and BNP in humans typically reflects a change in cardiac function. Specifically, the secretion of ANP is typically accelerated when the atrium undergoes a load, while the biosynthesis and secretion of BNP is stimulated when the ventricle undergoes a load. Thereupon, both ANP and BNP are useful as indicators in the diagnosis of heart disease. However, despite this and over time, BNP has become recognized as a useful indicator in the diagnosis of heart disease, more so than ANP. For example, the blood concentration of BNP is only $\frac{1}{6}$ of ANP in a normal subject but it becomes higher than ANP in patients of heart failure. Moreover, the blood concentration of BNP increases in the case of heart failure like ANP, and the plasma concentration of BNP often exceeds that of ANP, thus reflecting more accurately the severity of heart dysfunction. Moreover, BNP level in patients of heart failure sometimes increases to several tens times to several hundreds times of that of healthy normal subjects.

It is known that human proBNP, human NT-proBNP and hBNP can circulate and may be detected in test samples of patients suffering from cardiovascular disease, particularly heart failure. Both hBNP and human NT-proBNP are frequently used as markers to detect heart failure and to assess risk thereof in patients. However, the actual amount of each of the individual forms of BNP (i.e. human proBNP, human NT-proBNP and human BNP) that circulate is unclear due to the cross-reactivities of current commercial assays for these various forms (See, Liang F., et al., *J. American College of Cardiology*, 49(10):1071-1078 (2007)).

Additionally, it is known that human proBNP and human NT-proBNP can be glycosylated (See, Schellenberger, U. et al., *Archives of Biochemistry and Biophysics*, 451:160-166 (2006)), and these glycosylated forms have been isolated from human samples (See, Hammerer-Lercher A., et al., *Clinical Chemistry*, 54(5):858-865 (2008) and Seferian, K. et al., *Clinical Chemistry*, 54(5):866-873 (2008)). There are seven sites of possible glycosylation confined to a 36-amino acid region within the N terminal portion of the peptide (from amino acid 36 through 71). Antibodies generated to this region may or may not bind to samples containing analyte human proBNP or NT-proBNP, depending on: 1) the immunogen used to raise the antibody; and 2) whether or not the analyte is glycosylated. Optional assays for human proBNP and NT-proBNP should use antibodies that avoid these regions.

In view thereof, there is a need in the art for new assays that are capable of simultaneously quantifying the amount of human NT-proBNP, human proBNP and human BNP in a test sample. The present disclosure seeks to provide new assays and methods. The present disclosure also seeks to provide a kit for use in such assays and methods. The methods and kit can be used in qualitative or quantitative assays for human NT-proBNP, human proBNP and human BNP. These and other objects and advantages, as well as other additional features, will become apparent from the detailed description provided herein.

SUMMARY

In one embodiment, the present disclosure relates to an immunoassay for quantifying the amount of human NT-pro B-type natriuretic peptide ("human NT-proBNP"), human pro B-type natriuretic peptide ("human proBNP") and human brain natriuretic peptide ("hBNP") in a test sample being tested for or suspected of containing human NT-proBNP, human proBNP and hBNP. The method comprises the steps of:

(a) contacting a test sample (such as, for example, an aliquot derived or obtained from a test sample) with (i) a first capture antibody that binds to human NT-proBNP and that has been immobilized onto a solid phase to produce a first immobilized antibody and forming a first mixture comprising a first capture antibody-human NT-proBNP complex; (ii) a second capture antibody which that binds to human proBNP and that has been immobilized onto a solid phase to produce a second immobilized antibody and forming a second mixture comprising a second capture antibody-human proBNP complex; and (iii) the second capture antibody which in addition to binding human proBNP also binds to hBNP and that has been immobilized onto a solid phase to produce a third immobilized antibody and forming a third mixture comprising a second capture antibody-human hBNP complex, wherein said first capture antibody comprises antibody 15F11 and the second capture antibody comprises antibody 8.1;

(b) contacting said first mixture comprising the first capture antibody-human NT-proBNP complex with a first detection antibody which binds to human NT-proBNP and that has been conjugated to a detectable label to form a fourth mixture comprising a first capture antibody-human NT-proBNP-first detection antibody complex, wherein the first detection antibody 15C4;

(c) contacting said second mixture comprising the second capture antibody-human proBNP complex with the first detection antibody which in addition to binding human NT-proBNP also binds human proBNP, and that has been conjugated to a detectable label to form a fifth mixture comprising a second capture antibody-human proBNP-first detection antibody complex, wherein the first detection antibody 15C4;

(d) contacting said third mixture comprising the second capture antibody-human hBNP complex with a second detection antibody which binds to hBNP and that has been conjugated to a detectable label to form in a sixth mixture comprising a second capture antibody-hBNP-second detection antibody complex, wherein the second detection antibody is antibody 201.3;

(e) determining the amount of (i) first capture antibody-human NT-proBNP-first detection antibody complex formed in step (b) by detecting the detectable label as a measure of the amount of human NT-proBNP contained in the test sample; (ii) the second capture antibody-human proBNP-first detection antibody complex formed in step (c) by detecting the detectable label as a measure of the amount of human proBNP contained in the test sample; and (iii) the second capture antibody-hBNP-second detection antibody complex formed in step (d) by detecting the detectable label as a measure of the amount of hBNP contained in the test sample.

Alternatively, in the above method, a first aliquot obtained or derived from the test sample can be contacted with the first capture antibody to form the first capture antibody-human NT-proBNP complex. A second aliquot obtained or derived from the test sample can be contacted with the second capture antibody to form the second capture antibody-human proBNP complex. A third aliquot obtained or derived from the test sample can be contacted with the second capture antibody to form the second antibody-hBNP complex.

In the above immunoassay, the solid phase is selected from the group consisting of a magnetic particle, bead, test tube, microtiter plate, cuvette, membrane, a scaffolding molecule, film, filter paper, disc, and chip.

In the above immunoassay, the detectable label of the first detection antibody is selected from the group consisting of a radioactive label, an enzymatic label, a chemiluminescent label, a fluorescent label, a thermometric label, and an immuno-polymerase chain reaction label. The detectable label of the second detection antibody is selected from the group consisting of a radioactive label, an enzymatic label, a chemiluminescent label, a fluorescent label, a thermometric label, and an immuno-polymerase chain reaction label.

In another aspect, the present disclosure immunoassay relates to a method for quantifying the amount of human NT-proBNP, human proBNP and hBNP in a test sample being tested for or suspected of containing human NT-proBNP, human proBNP and hBNP. The method comprises the steps of:

(a) contacting a test sample with (i) a first detection antibody which binds to human NT-proBNP and that has been conjugated to a detectable label to form a first mixture comprising a human NT-proBNP-first detection antibody complex; (ii) the first detection antibody which, in addition to binding to human NT-proBNP, also binds to human proBNP, and that has been conjugated to a detectable label to form a second mixture comprising a human proBNP-first detection antibody complex; and (iii) a second detection antibody which binds to hBNP and that has been conjugated to a detectable label to further form in a third mixture comprising a hBNP-second detection antibody complex, wherein the first detection antibody is antibody 15C4 and the second detection antibody is antibody 201.3;

(b) contacting said first mixture comprising the human NT-proBNP-first detection antibody complex with a first capture antibody that binds to human NT-proBNP and that has been immobilized onto a solid phase to produce a first immobilized antibody to form a fourth mixture comprising a first capture antibody-human NT-proBNP-first detection antibody complex, wherein said first capture antibody comprises antibody 15F11;

(c) contacting the second mixture comprising the human proBNP-first detection antibody complex with a second capture antibody which binds to human proBNP and that has been immobilized onto a solid phase to produce a second immobilized antibody to form a fifth mixture comprising a second capture antibody-human proBNP-first detection antibody complex, wherein said second capture antibody comprises antibody 8.1;

(d) contacting the third mixture comprising the hBNP-second detection antibody complex with a second capture antibody which, in addition to binding to human proBNP, also binds to hBNP, and that has been immobilized onto a solid phase to produce a third immobilized antibody to form a sixth mixture comprising a second capture antibody-hBNP-second detection antibody complex; wherein said second capture antibody comprises antibody 8.1; and (e) determining the amount of (i) first capture antibody-human NT-proBNP-first detection antibody complex formed in step (b) by detecting the detectable label as a measure of the amount of human NT-proBNP contained in the test sample; (ii) the second capture antibody-human proBNP-first detection antibody complex formed in step (c) by detecting the detectable label as a measure of the amount of human proBNP contained in the test sample; and (iii) the second capture antibody-hBNP-second detection antibody complex formed in step (d) by detecting the detectable label as a measure of the amount of hBNP contained in the test sample.

Alternatively, in the above method, a first aliquot obtained or derived from the test sample can be contacted with the first detection antibody to form the human NT-proBNP-first detection antibody complex. A second aliquot obtained or derived from the test sample can be contacted with the first detection antibody to form the human proBNP-first detection antibody complex. A third aliquot obtained or derived from the test sample can be contacted with the second detection antibody to form the hBNP-second detection antibody complex.

In the above immunoassay, the solid phase is selected from the group consisting of a magnetic particle, bead, test tube, microtiter plate, cuvette, membrane, a scaffolding molecule, film, filter paper, disc, and chip.

In the above immunoassay, the detectable label of the first detection antibody is selected from the group consisting of a radioactive label, an enzymatic label, a chemiluminescent label, a fluorescent label, a thermometric label, and an immuno-polymerase chain reaction label. The detectable label of the second detection antibody is selected from the group consisting of a radioactive label, an enzymatic label, a chemiluminescent label, a fluorescent label, a thermometric label, and an immuno-polymerase chain reaction label.

In still yet another aspect, the present disclosure relates to an immunodiagnostic reagent. Specifically, the immunodiagnostic reagent of the present disclosure comprises:

(a) a first capture antibody specific for human NT-pro B-type natriuretic peptide ("human NT-proBNP");

(b) a second capture antibody which is specific to each of human pro B-type natriuretic peptide ("human proBNP") and human brain natriuretic peptide ("hBNP");

(c) a first detection antibody which is specific to each of human NT-proBNP and human proBNP; and (d) a second detection antibody which is specific to hBNP.

An example of a first capture antibody that can be used as an immunodiagnostic reagent is antibody 15F11. An example of a second capture antibody that can be used as an immunodiagnostic reagent is antibody 8.1.

An example of a first detection antibody that can be used as an immunodiagnostic reagent is antibody 15C4. An example of a second detection antibody that can be used as an immunodiagnostic reagent is antibody 201.3.

In still yet another aspect, the present disclosure relates to a kit for use in an assay for quantifying or detecting the amount of human NT-proBNP, human proBNP and hBNP in a test sample, said kit comprising:

(a) instructions for conducting the assay of the test sample; and (b) immunodiagnostic reagents comprising:
(i) a first capture antibody specific for human NT-proBNP;
(ii) a second capture antibody which is specific to each of human proBNP and hBNP;
(iii) a first detection antibody which is specific to each of human NT-proBNP and human proBNP; and
(iv) a second detection antibody which is specific to hBNP.

An example of a first capture antibody that can be used as an immunodiagnostic reagent in the above kit is antibody 15F11. An example of a second capture antibody that can be used as an immunodiagnostic reagent in the above kit is antibody 8.1.

An example of a first detection antibody that can be used as an immunodiagnostic reagent in the above kit is antibody 15C4. An example of a second detection antibody that can be used as an immunodiagnostic reagent in the above kit is antibody 201.3.

DESCRIPTION OF THE FIGURES

FIGS. 1A, 1B and 1C show the results of the immunoassay of the present disclosure as described in Example 1.

FIGS. 2A and 2B shows the epitopes detected using the immunoassay of the present disclosure as described in Example 1.

DETAILED DESCRIPTION

Figure 1C:
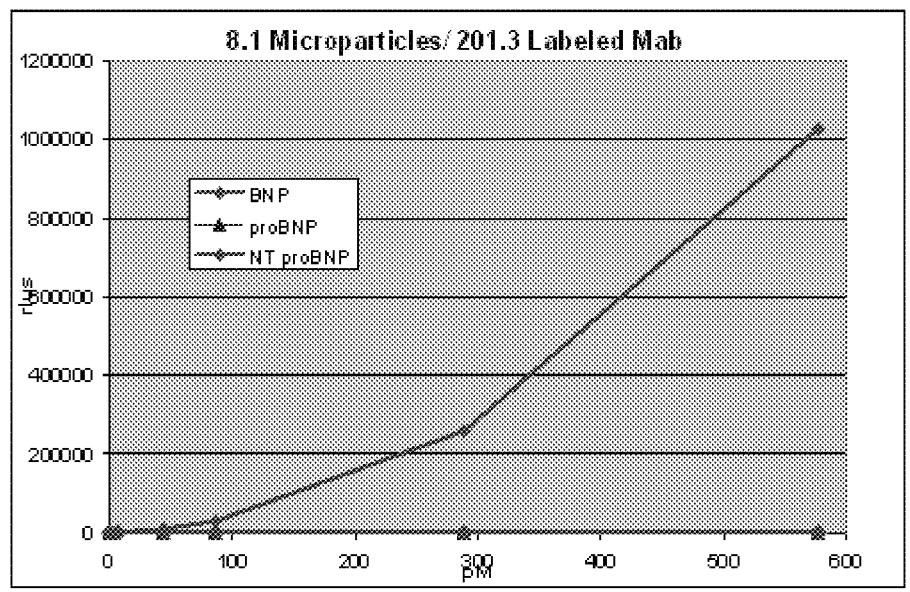

The present disclosure relates to immunoassays for simultaneously detecting or quantifying the amount of: (1) human NT-pro B-type natriuretic peptide ("human NT-proBNP"); (2) human pro B-type natriuretic peptide ("human proBNP"); and (3) human B-type natriuretic peptide ("hBNP") present in a test sample being tested for or suspected of containing human NT-proBNP, human proBNP and hBNP. In yet another embodiment, the present disclosure relates to immunodiagnostic reagents comprising at least one first capture antibody specific for human NT-proBNP; at least one second capture which is specific to each of human proBNP and hBNP, at least one first detection antibody which is specific to each of human NT-proBNP and human proBNP and at least one second detection antibody which is specific to hBNP. In still yet another embodiment, the present disclosure relates to a kit for performing an immunoassay. Such kits can comprise instructions for conducting such an immunoassay and the above described immunodiagnostic reagents.

A. Definitions

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

a) Antibody

As used herein, the terms "antibody" and "antibodies" refer to monoclonal antibodies, multispecific antibodies, human antibodies, humanized antibodies (fully or partially humanized), animal antibodies (in one aspect, a bird (for example, a duck or goose), in another aspect, a shark or whale, in yet another aspect, a mammal, including a non-primate (for example, a cow, pig, camel, llama, horse, goat, rabbit, sheep, hamsters, guinea pig, cat, dog, rat, mouse, etc)

and a non-human primate (for example, a monkey, such as a cynomologous monkey, a chimpanzee, etc)), recombinant antibodies, chimeric antibodies, single-chain Fvs (scFv), single chain antibodies, single domain antibodies, Fab fragments, F(ab') fragments, Fab" fragments, disulfide-linked Fvs (sdFv), and anti-idiotypic (anti-Id) antibodies (including, for example, anti-Id antibodies to antibodies of the present disclosure), and functionally active epitope-binding fragments of any of the above. In particular, antibodies include immunoglobulin molecules and immunologically active fragments of immunoglobulin molecules, namely, molecules that contain an antigen binding site. Immunoglobulin molecules can be of any type (for example, IgG, IgE, IgM, IgD, IgA and IgY), class (for example, $IgG_1$, $IgG_2$, $IgG_3$, $IgG_4$, $IgA_1$ and $IgA_2$) or subclass.

b) 15C4

As used herein, the term "15C4" refers to an IgG1 monoclonal antibody that is available from HyTest (Turku, Finland) (Cat. #4NT1) that binds to amino acid residues 63-71 of SEQ ID NO:3.

c) 15F11

As used herein, the term "15F11" refers to an IgG2b monoclonal antibody that is available from HyTest (Turku, Finland) (Cat. #4NT1) that binds to amino acid residues 13-24 of SEQ ID NO:3.

d) 24E11

As used herein, the term "24E11" refers to an IgG2a monoclonal antibody that is available from HyTest (Turku, Finland) (Cat. #4NT1) that binds to amino acid residues 67-76 of SEQ ID NO:3.

e) 8.1

As used herein, "8.1" refers to a monoclonal antibody or derivatives thereof produced by hybridoma cell line 8.1 which has been deposited with the American Type Culture Collection (A.T.C.C.) on Feb. 21, 1996 and assigned A.T.C.C. Accession No. HB-12056. 8.1 and methods for making 8.1 are described in U.S. Pat. No. 6,162,902, the contents of which are herein incorporated by reference. 8.1 binds to an epitope comprising amino acid residues 26-32 on hBNP.

f) 201.3

As used herein, "201.3" refers to a monoclonal antibody or derivatives thereof produced by hybridoma cell line 201.3 which has been deposited with the A.T.C.C. on Feb. 14, 1996 and assigned A.T.C.C. Accession No. HB-12045. 201.3 and methods for making 201.3 are described in U.S. Pat. No. 6,162,902, the contents of which are herein incorporated by reference. 201.3 binds to an epitope comprising amino acid residues 1-10 on hBNP.

g) Epitope

As used herein, the term "epitope" or "epitopes" refers to sites or fragments of a polypeptide or protein having antigenic or immunogenic activity in a subject. An epitope having immunogenic activity is a site or fragment of a polypeptide or protein that elicits an antibody response in an animal. An epitope having antigenic activity is a site or fragment of a polypeptide or protein to which an antibody immunospecifically binds as determined by any method well-known to those skilled in the art, for example by immunoassays.

h) Human Brain Natriuretic Peptide

As used herein, the terms "human brain natriuretic peptide", "human BNP", "hBNP", "hBNP-32", "hBNP peptide", "hBNP polypeptide", or "B-type natriuretic peptide" used interchangeably herein, refer to a 32 amino acid molecule having the amino acid sequence shown in SEQ ID NO:4. The amino acid sequence shown in SEQ ID NO:4 is represented by amino acid residues 77-108 of the 108 amino acid sequence of human proBNP (SEQ ID NO:2).

i) Immunodiagnostic Reagent

As used herein, the term "immunodiagnostic reagent" refers to one or more antibodies that specifically bind to a region (e.g., epitope) of human NT-proBNP, (2) human proBNP, (3) human BNP, or (4) any combinations of (1), (2) or (3).

j) Pre-Pro Peptide Precursor of Human BNP

As used herein, the term "pre-pro peptide precursor of human BNP" or "human pre-proBNP" refers to a 134 amino acid molecule having the amino acid sequence shown in SEQ ID NO:1.

k) Human Pro B-Type Natriuretic Peptide

As used herein, the phrase "human pro B-type natriuretic peptide" or "human proBNP" refers to a 108 amino acid molecule having the amino acid sequence shown in SEQ ID NO:2. Human proBNP is derived from human pre-proBNP.

l) Human N-Terminal-pro B-type Natriuretic Peptide

As used herein, the phrase "Human N-terminal-pro B-type natriuretic peptide" or "human NT-proBNP", refers to a 76 amino acid molecule having the amino acid sequence shown in SEQ ID NO:3. Human NT-proBNP is derived from human proBNP (SEQ ID NO:2).

m) Subject

As used herein, the terms "subject" and "patient" are used interchangeably, although a subject of the disclosure herein need not necessarily be undergoing or have undergone medical treatment at the time of the immunoassay. As used herein, the terms "subject" and "subjects" refer to an animal, in one aspect, a bird (for example, a duck or goose), in another aspect, a shark or whale, or in a further aspect, a mammal including, a non-primate (for example, a cow, pig, camel, llama, horse, goat, rabbit, sheep, hamsters, guinea pig, cat, dog, rat, and mouse) and a primate (for example, a monkey, such as a cynomologous monkey, chimpanzee, and a human). Preferably, the subject is a human.

n) Test Sample

As used herein, the term "test sample" refers to a biological sample derived from tissues, serum, plasma, whole blood, lymph, CNS fluid, urine or other bodily fluids of a subject that is being tested for, and/or may be suspected of containing human NT-proBNP, proBNP and hBNP. The test sample can be prepared using routine techniques known to those skilled in the art.

B. Immunoassays and Immunodiagnostic Reagents

As mentioned briefly herein, in one embodiment, the present disclosure relates to immunoassays for the simultaneous qualitative detection and/or quantification of (1) human NT-proBNP; (2) human proBNP; and (3) hBNP in a test sample. The immunoassays of the present disclosure provide a number of benefits. First, the immunoassays of the present disclosure allow for the simultaneous and specific detection of (1) human NT-proBNP; (2) human proBNP; and (3) hBNP in a test sample. Second, the immunoassays of the present disclosure allow for the evaluation of (1) human NT-proBNP; (2) human proBNP; and (3) hBNP both individually and in relationship to one in another in the same (or single) test sample (aliquots derived or obtained from a single test sample can be used in the methods of the present invention). Third, the immunoassays of the present disclosure only require two capture antibodies and two detection antibodies to detect three different analytes (namely, (1) human NT-proBNP; (2) human proBNP; and (3) hBNP) in a test sample thus reducing the cost associated with performing such an immunoassay.

The immunoassays of the present disclosure can be conducted using any format known in the art, such as, but not limited to, a sandwich format. Moreover, the immunoassays of the present disclosure are performed in multiple reaction vessels. In an exemplary format, the immunoassays of the present disclosure are performed in three separate reaction vessels. In other words, the immunoassay for human NT-proBNP is performed in one reaction vessel, the immunoassay for human proBNP is performed in one reaction vessel (which would be a second reaction vessel) and the immunoassay for hBNP is performed in one reaction vessel (which would be a third reaction vessel).

In certain embodiments of the present disclosure, two capture antibodies and two detection antibodies are employed to separate and quantify human (1) NT-proBNP; (2) human proBNP; and (3) hBNP in a test sample. More specifically, the two capture antibodies and two detection antibodies bind to certain epitopes of (1) human NT-proBNP; (2) human proBNP; and (3) hBNP forming immune complexes referred to as a "sandwich". Generally, in the immunoassays two antibodies are used to capture the (1) human NT-proBNP; (2) human proBNP; and (3) hBNP in the test sample (these antibodies are frequently referred to as a "capture" antibody or "capture" antibodies) and two antibodies are used to bind a detectable (namely, quantifiable) label to the sandwich (these antibodies are frequently referred to as the "detection antibody," "detection antibodies," a "conjugate" or "conjugates").

The inventors have discovered that excellent immunoassays, particularly, sandwich assays, can be performed using certain combinations of antibodies as the capture and detection antibodies. More specifically, a first capture antibody is used that binds to human NT-proBNP. An example of such an antibody that can be used as the first capture antibody is antibody 15F11. In addition, a second capture antibody that binds to each of (1) human proBNP; and (2) hBNP is also used. An example of a second capture antibody that can be used is antibody 8.1.

As mentioned previously herein, two detection antibodies are used in the present disclosure. The first detection antibody binds to each of (1) human NT-proBNP; and (2) human proBNP. An example of a first detection antibody that can be used is antibody 15C4. In addition, the second detection antibody is an antibody that binds to hBNP. An example of a second detection antibody that can be used is antibody 201.3.

The test sample being tested for (e.g., suspected of containing) (1) human NT-proBNP; (2) human proBNP; and (3) hBNP can be contacted with the two capture antibodies and the two detection antibodies either simultaneously or sequentially and in any order. Alternatively, any number of aliquots derived from the test sample can be tested (such as, but not limited to, at least three (3) aliquots derived from the test sample). For example, the test sample can be first contacted with at least one capture antibody and then (sequentially) with at least one detection antibody. Alternatively, the test sample can be first contacted with at least one detection antibody and then (sequentially) with at least one capture antibody. In yet another alternative, the test sample can be contacted simultaneously with a capture antibody and a detection antibody.

In the sandwich assay format, a test sample suspected of containing (1) human NT-proBNP; (2) human proBNP and (3) hBNP is first brought into contact with the above described two capture antibodies under conditions which allow the formation of the following complexes: (a) a first capture antibody-human NT-proBNP complex (such as in a first mixture); (b) a second capture antibody-human proBNP complex (such as in a second mixture); and (c) a second capture antibody-hBNP complex (such as in a third mixture). Separate aliquots (e.g., at least three aliquots) of the test sample can be used to form the first capture antibody-human NT-proBNP complex, the second capture antibody-human proBNP complex and the second capture antibody-hBNP complex. As mentioned previously herein, at least one first capture antibody is used that binds to a human NT-proBNP. An example of such a first capture antibody is 15F11. The second capture antibody binds to each of (1) human proBNP; and (2) hBNP. An example of such a second capture antibody is antibody 8.1. The order in which the capture antibodies are brought into contact with the test sample to form the above described complexes is not critical. Alternatively, the test sample can be contacted simultaneously with each of the capture antibodies (in separate reaction vessels). In a sandwich assay, the antibodies, preferably, the two capture antibodies, are used in molar excess amounts of the maximum amount of (1) human NT-proBNP; (2) human proBNP; and (3) hBNP expected in the test sample. For example, from about 5 µg/mL to about 1 mg/mL of antibody per mL of buffer (e.g., microparticle coating buffer) can be used.

Optionally, prior to contacting the test sample with the two capture antibodies, at least one of capture antibodies can be bound to a solid support which facilitates the separation of the above described complexes (namely, (a) a first capture antibody-human NT-proBNP complex; (b) a second capture antibody-human proBNP complex; and (c) a second capture antibody-hBNP complex) from the test sample. Still further optionally, prior to contacting the test sample with the two capture antibodies, all of the capture antibodies can be bound to a solid support which facilitates the separation of the above described complexes (namely, (a) a first capture antibody-human NT-proBNP complex; (b) a second capture antibody-human proBNP complex; and (c) a second capture antibody-hBNP complex) from the test sample. Any solid support known in the art can be used, including but not limited to, solid supports made out of polymeric materials in the forms of wells, tubes or beads. The antibodies can be bound to the solid support by adsorption, by covalent bonding using a chemical coupling agent or by other means known in the art, provided that such binding does not interfere with the ability of the antibody to bind to (1) human NT-proBNP (2) human proBNP; and (3) hBNP. Alternatively, the antibodies can be bound with microparticles that have previously been coated with streptavidin (for example, using Power-Bind™-SA-MP streptavidin coated microparticles, available from Seradyn, Indianapolis, Ind.). Alternatively, the antibodies can be bound using microparticles that have been previously coated with anti-species specific monoclonal antibodies. Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl)carbodiimide.

After the test sample being tested for and/or suspected of containing (1) human NT-proBNP; (2) human proBNP; and (3) hBNP is brought into contact with the two capture antibodies, the mixtures are incubated in order to allow for the formation of a mixture containing at least the following complexes: (a) a first capture antibody-human NT-proBNP complex (the first mixture); (b) a second capture antibody-human proBNP complex (the second mixture); and (c) a second capture antibody-hBNP complex (the third mixture). The incubation can be carried out at a pH of from about 4.5 to about 10.0, at a temperature of from about 2° C. to about 45° C., and for a period from at least about one (1) minute to about eighteen (18) hours, preferably from about 1 to 20 minutes, most preferably from about 2-4 minutes. The immunoassay described herein can be conducted in one step (meaning the test sample, at least three capture antibodies and at least three detection antibodies are all added sequentially or simultaneously to a reaction vessel) or in more than one step, such as two steps, three steps, etc.

After formation of the mixtures containing the first capture antibody-human NT-proBNP complex, the second capture antibody-human proBNP complex and a second capture antibody-hBNP complex, the complexes are then contacted with two detection antibodies under conditions which allow for the formation of a first capture antibody-human NT-proBNP first detection antibody complex (thus forming a fourth mixture), a second capture antibody-human proBNP first detection antibody complex (thus forming a fifth mixture) and a second capture antibody-hBNP second detection antibody complex (thus forming a sixth mixture). The detection antibody used to detect the first capture antibody-human NT-proBNP complex and the second capture antibody-human proBNP complex are identical to one another. As with the capture antibody (e.g., the first capture antibody), when the at first detection antibody is brought into contact with the capture antibody-human NT-proBNP complex, the first detection antibody is brought into contact with the second capture antibody-human proBNP complex and the second detection antibody is brought into contact with the capture antibody-hBNP complex a period of incubation under conditions similar to those described above is required for the formation of the first capture antibody-human NT-proBNP-first detection antibody complex, a second capture antibody-human proBNP-first detection complex, a second capture antibody-hBNP-second detection antibody complex or combinations thereof. Preferably, at least one of the two detection antibodies contain a detectable label. Most preferably, both detection antibodies contain a detectable label. The detectable label can be bound to the at least one detection antibody (e.g., the first detection antibody) prior to, simultaneously with or after the formation of the first capture antibody-human NT-proBNP-first detection antibody complex. Any detectable label known in the art can be used. For example, the detectable label can be a radioactive label, such as, $^3H$, $^{125}I$, $^{35}S$, $^{14}C$, $^{32}P$, $^{33}P$ an enzymatic label, such as horseradish peroxidase, alkaline phosphatase, glucose 6-phosphate dehydrogenase, etc., a chemiluminescent label, such as, acridinium esters, luminol, isoluminol, thioesters, sulfonamides, phenanthridinium esters, etc. a fluorescence label, such as, fluorescein (5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, etc.), rhodamine, phycobiliproteins, R-phycoerythrin, quantum dots (zinc sulfide-capped cadmium selenide), a thermometric label or an immuno-polymerase chain reaction label. An introduction to labels, labeling procedures and detection of labels is found in Polak and Van Noorden, *Introduction to Immunocytochemistry*, 2$^{nd}$ ed., Springer Verlag, N.Y. (1997) and in Haugland, *Handbook of Fluorescent Probes and Research Chemicals* (1996), which is a combined handbook and catalogue published by Molecular Probes, Inc., Eugene, Oreg. In addition, more than one label can be used. For example, double conjugates can be used, each of which contain different labels. For example, one conjugate antibody can contain biotin and the second conjugate can be an anti-biotin antibody labeled with acridinium. Other variations would be easily recognized by one of ordinary skill in the art.

The detectable label can be bound to the antibodies either directly or through a coupling agent. An example of a coupling agent that can be used is EDAC (1-ethyl-3-(3-dimethylaminopropyl) carbodiimide, hydrochloride) that is commercially available from Sigma-Aldrich, St. Louis, Mo. Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as, N10-(3-sulfopropyl)-N-(3-carboxypropyl)-acridinium-9-carboxamide active esters, otherwise known as CPSP-Acridinium Ester or N10-(3-sulfopropyl)-N-(3-sulfopropyl)-acridinium-9-carboxamide active ester, otherwise known as SPSP-Acridinium Ester.

Any or all of the first capture antibody-human NT-proBNP-first detection antibody complex, a second capture antibody-human proBNP-first detection complex, a second capture antibody-hBNP-second detection antibody complex can be, but do not have to be, separated from the remainder of the test sample prior to quantification of the label. For example, if the at least one capture antibody (e.g., the first capture antibody) is bound to a solid support, such as a well or a bead, separation can be accomplished by removing the fluid (of the test sample) from contact with the solid support. Alternatively, if the first capture antibody is bound to a solid support it can be simultaneously contacted with the human NT-proBNP-containing sample and the first detection antibody to form a first capture antibody-human NT-proBNP-first antibody complex, followed by removal of the fluid (test sample) from contact with the solid support. If the first capture antibody is not bound to a solid support, then the first capture antibody-human NT-proBNP-first detection antibody complex does not have to be removed from the test sample for quantification of the amount of the label. Alternatively, if the second capture antibody is bound to a solid support it can be simultaneously contacted with the human capture proBNP-containing sample and the first detection antibody to form a second capture antibody-human-proBNP-second antibody complex, followed by removal of the fluid (test sample) from contact with the solid support. If the second capture antibody is not bound to a solid support, then the second capture antibody-human proBNP-first detection antibody complex does not have to be removed from the test sample for quantification of the amount of the label. Alternatively, if the second capture antibody is bound to a solid support it can be simultaneously contacted with the hBNP-containing sample and a second detection antibody to form a second capture antibody-hBNP-second antibody complex, followed by removal of the fluid (test sample) from contact with the solid support. If the at least one second capture antibody is not bound to a solid support, then the second capture antibody-hBNP-second detection antibody complex does not have to be removed from the test sample for quantification of the amount of the label.

After formation of the labeled first capture antibody-human NT-proBNP first detection antibody complex, the labeled second capture antibody-human proBNP first detection antibody complex and the labeled second capture antibody-hBNP second detection antibody complex, the amount of label in each of the complexes (and hence each of the fourth, fifth and sixth mixtures) is quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength")

and detecting another color (which is known as the "emission wavelength") that is emitted by the label in response to the stimulation. If the label is a chemiluminescent label, the label is quantified detecting the light emitted either visually or by using luminometers, x-ray film, high speed photographic film, a CCD camera, etc. Once the amount of the label in the complex has been quantified, the concentration of human NT-proBNP, human proBNP and hBNP in the test sample is determined by use of a standard curve that has been generated using serial dilutions of human NT-proBNP of known concentration, human proBNP or hBNP. Other than using serial dilutions of human NT-proBNP, human proBNP or hBNP the standard curve can be generated gravimetrically, by mass spectroscopy and by other techniques known in the art.

In another embodiment, the present disclosure relates to immunodiagnostic reagents. Specifically, the at least one capture antibody (namely, an antibody that binds to an epitope comprising or consisting of amino acid residues 13-24 of SEQ ID NO:3) and at least one detection antibody (namely, an antibody that binds to an epitope comprising or consisting of amino acid residues 63-71 of SEQ ID NO:3 or amino acid residues 67-76 of SEQ ID NO:3) described herein can be used individually or in combination, as one or more immunodiagnostic reagents in one or more immunoassays, such as those described above. When the at least one capture antibody and at least one detection antibody described herein are used together in an immunoassay (such as those described previously herein), the immunoassay exhibits a cross-reactivity of less than about 1.0% with any human proBNP in a test sample. More specifically, the immunoassay exhibits less than about 0.9%, less than about 0.8%, less than about 0.7%, less than about 0.6%, less than about 0.5%, less than about 0.4%, less than about 0.3%, less than about 0.2%, less than about 0.1% or less than about 0.001% with any human proBNP that may be present in the test sample.

Alternatively, at least one capture antibody (namely, an antibody that binds to one epitope comprising or consisting of amino acid residues 103-108 of SEQ ID NO:2) and at least one detection antibody (namely, an antibody that binds to an epitope comprising or consisting of 63-71 of SEQ ID NO:2) described herein can be used individually or in combination, as one or more immunodiagnostic reagents in one or more immunoassays, such as those described above.

Alternatively, at least one capture antibody (namely, an antibody that binds to one epitope comprising or consisting of amino acid residues 28-32 of SEQ ID NO:4) and at least one detection antibody (namely, an antibody that binds to an epitope comprising or consisting of 1-10 of SEQ ID NO:4) described herein can be used individually or in combination, as one or more immunodiagnostic reagents in one or more immunoassays, such as those described above.

C. Adaptations of the Methods

The disclosure herein also can be adapted for use in a variety of automated and semi-automated systems (including those wherein the solid phase comprises a microparticle), as described, e.g., in U.S. Pat. Nos. 5,089,424 and 5,006,309, and as, e.g., commercially marketed by Abbott Laboratories (Abbott Park, Ill.) including but not limited to Abbott's ARCHITECT®, AxSYM®, IMx®, PRISM®, and Quantum™ II instruments, as well as other platforms. Moreover, the disclosure optionally is adaptable for the Abbott Laboratories commercial Point of Care (i-STAT™) electrochemical immunoassay system for performing sandwich immunoassays. Immunosensors, and their methods of manufacture and operation in single-use test devices are described, for example in, U.S. Pat. No. 5,063,081, U.S. Patent Application 2003/0170881, U.S. Patent Application 2004/0018577, U.S. Patent Application 2005/0054078, and U.S. Patent Application 2006/0160164, which are incorporated in their entireties by reference for their teachings regarding same.

D. Exemplary Kits

The present disclosure herein also can be adapted for use in a variety of kits for use on automated and semi-automated systems and platforms, e.g., commercially marketed by Abbott Laboratories (Abbott Park, Ill.) including, but not limited to, Abbott Laboratories' ARCHITECT®, AxSYM®, IMx®, PRISM®, and Quantum™ II instruments, Abbott Laboratories' commercial Point of Care (i-STAT™) electrochemical immunoassay system for performing sandwich immunoassays, as well as other platforms.

Such kits can comprise one or more of the immunodiagnostic reagents (e.g., the capture and detection antibodies) described herein. More specifically, if the kit is a kit for performing an immunoassay, the kit can optionally contain (1) at least two capture antibodies and two detection antibodies that bind to human NT-proBNP, human proBNP and human BNP; and (2) one or more instructions for performing the immunoassay. The immunodiagnostic reagents of the present disclosure can be included in such a test kit as a capture antibody, as a detection antibody or both as a capture antibody and a detection antibody. For example, antibody 15F11 can be included in the kit as capture antibody and antibody 15C4 can be included in the kit as a detection antibody. Alternatively, antibody 15F11 can be included in the kit as a capture antibody and antibody 24E11 can be included in the kit as a detection antibody. Optionally, the kit can also contain at least one calibrator or control. Any calibrator or control can be included in the kit. Preferably, however, the calibrator or control is human NT-proBNP, especially SEQ ID NO: 3, human proBNP, especially SEQ ID NO:4, hBNP, especially SEQ ID NO:2 or combinations thereof as described previously herein. Accordingly, the kits can comprise at least one calibrator, or at least one control, or a combination of at least one calibrator and at least one control.

Optionally the kits also can include quality control reagents (e.g., sensitivity panels, calibrators, and positive controls). Preparation of quality control reagents is well known in the art, and is described, e.g., on a variety of immunodiagnostic product insert sheets. Human NT-proBNP, human proBNP, hBNP or combinations thereof sensitivity panel members optionally can be prepared in varying amounts containing, e.g., known quantities of human NT-proBNP antigen, human proBNP antigen, hBNP antigen or combinations thereof ranging from "low" to "high", e.g., by spiking known quantities of the human NT-proBNP antigen, human proBNP, hBNP or combinations thereof into an appropriate assay buffer (e.g., a phosphate buffer). These sensitivity panel members optionally are used to establish assay performance characteristics, and further optionally are useful indicators of the integrity of the immunoassay kit reagents, and the standardization of assays. The human NT-proBNP antigen, human proBNP antigen, hBNP antigen or combinations thereof also can be employed as calibrators.

The antibodies provided in the kit can incorporate a detectable label, such as a fluorophore, radioactive moiety, enzyme, biotin/avidin label, chromophore, chemiluminescent label, or the like, or the kit may include reagents for labeling the antibodies or reagents for detecting the antibodies (e.g., detection antibodies) and/or for labeling the antigens or reagents for detecting the antigen. The antibodies, calibrators and/or controls can be provided in separate containers or pre-dispensed into an appropriate assay format, for example, into microtiter plates.

In yet another embodiment, the kit can comprise, either alone, with instructions, or with other aspects of the kit and kit components, an immunodiagnostic agent that comprises one or more antibodies selected from the group consisting of 15F11, 15C4, 8.1, 201.3 and 24E11.

The kits can optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), may also be included in the kit. The kit may additionally include one or more other controls. One or more of the components of the kit may be lyophilized and the kit may further comprise reagents suitable for the reconstitution of the lyophilized components.

The various components of the kit optionally are provided in suitable containers. As indicated above, one or more of the containers may be a microtiter plate. The kit further can include containers for holding or storing a sample (e.g., a container or cartridge for a blood or urine sample). Where appropriate, the kit may also optionally contain reaction vessels, mixing vessels and other components that facilitate the preparation of reagents or the test sample. The kit may also include one or more instruments for assisting with obtaining a test sample, such as a syringe, pipette, forceps, measured spoon, or the like.

The kit further can optionally include instructions for use, which may be provided in paper form or in computer-readable form, such as a disc, CD, DVD or the like.

Now by way of example, and not of limitation, examples of the present disclosure shall now be given.

EXAMPLE 1

Simultaneous Detection and Quantification of Human Nt-Pro B-Type Natriuretic Peptide, Human Pro B-Type Natriuretic Peptide and Human B-Type Natriuretic Peptide Materials, Methods and Results In this example, an automated ARCHITECT® System (Abbott Laboratories, Abbott Park, Ill.) was used to perform immunoassays that would quantitate human NT-proBNP, human proBNP and human BNP. The detection of these three analytes is accomplished using two types of monoclonal antibody coated magnetic microparticles and two types of labeled monoclonal antibodies.

Dilutions of human NT proBNP (HyTest, Turku, Finland; Catalog No. 8NT1) containing human NT proBNP (0.0 pM-577.4 pM) in 10 mM NaOAc, 10 mM DTPA, 2% BSA, 0.1% ProClin 300, 0.1% NaN3, pH 5.6 (Abbott Laboratories, Abbott Park, Ill.) were tested. Testing was performed in reaction vessels (Abbott Laboratories, Abbott Park, Ill.) that are used for individual tests in the automated ARCHITECT® System. All the described steps took place in the ARCHITECT® instrument.

Dilutions of human proBNP (HyTest, Turku, Finland; Catalog No. 8PRO8) containing human proBNP (0.0 pM-577.4 pM) in 10 mM NaOAc, 10 mM DTPA, 2% BSA, 0.1% ProClin 300, 0.1% NaN3, pH 5.6 (Abbott Laboratories, Abbott Park, Ill.) were tested. Testing was performed in reaction vessels (Abbott Laboratories, Abbott Park, Ill.) that are used for individual tests in the automated ARCHITECT® System. All the described steps took place in the ARCHITECT® instrument.

Human BNP Architect BNP Calibrators (List 8K2802, Abbott Laboratories, Abbott Park, Ill.) (0.0 pM-577.4 pM) were tested. Testing was performed in reaction vessels (Abbott Laboratories, Abbott Park, Ill.) that are used for individual tests in the automated Abbott ARCHITECT® System. All the described steps took place in the ARCHITECT® instrument.

These samples were tested using a traditional two-step immunoassay format, as described. The two-step assay format occurs in a single reaction vessel. The two-step assay format comprises the steps of adding the sample, adding antibody coated magnetic microparticles, binding analyte, washing magnetic microparticle-analyte complexes, adding labeled conjugate antibody, binding of labeled conjugate to magnetic microparticle-analyte complexes, washing the resulting magnetic microparticle-analyte-labeled conjugate antibody complexes, and reading signal generated by the complexed label remaining in the reaction vessel.

Human BNP Detection

Each sample dilution was dispensed in the amount of 100 μL into the individual reaction vessels. At the same time, 0.10% EDAC-coated magnetic microparticles (50 μL) (Polymer Laboratories Ltd, now part of Varian. Inc., Shropshire. UK) coated with anti-human BNP/human proBNP monoclonal antibody 8.1 (Scios, Sunnyvale, Calif.; A.T.C.C. Accession No. HB-12056) were dispensed in the amount of 50 μL into the same reaction vessel. The reaction vessel was then vortexed to mix the sample and magnetic microparticles. Each reaction mixture was incubated for 18 minutes at 37° C.

During this incubation, any human BNP in the samples was captured by monoclonal antibody 8.1 that were coated onto the magnetic microparticles.

Upon completion of the 18 minute incubation, the monoclonal antibody 8.1 coated magnetic microparticles and monoclonal antibody 8.1/BNP complexes were magnetically captured and immobilized into a pellet on the side of the reaction vessel. The immobilized magnetic microparticles and monoclonal antibody 8.1/BNP complex pellet were then washed by alternately aspirating the liquid from the vessel, and then adding assay kit wash buffer (ARCHITECT® wash buffer, available from Abbott Laboratories, Abbott Park, Ill.) into the reaction vessel (1 mL wash buffer, repeated 4 times). This process removed any unbound human BNP from the reaction mixture. The magnetically captured microparticle, human BNP monoclonal antibody 8.1/BNP complexes formed during the 18 minute incubation remained in the reaction vessel. The magnetic microparticle monoclonal antibody 8.1/human BNP complex pellet was then released.

During a second incubation of 4 minutes, anti-human BNP/anti-human proBNP, acridinium (Abbott Laboratories, Abbott Park) labeled monoclonal antibody 201.3 (Scios, Sunnyvale, Calif.; A.T.C.C. Accession No. HB-12045) was dispensed in the amount of 50 μL into individual reaction vessels containing only the monoclonal antibody 8.1 coated magnetic microparticles and monoclonal antibody 8.1/BNP complexes. This reaction mixture was then vortexed to disperse the microparticle pellet.

The magnetic microparticles and monoclonal antibody 8.1/BNP complexes were incubated with the acridinium (Abbott Laboratories, Abbott Park, Code 88333) labeled anti-human BNP 201.3 monoclonal antibodies, in buffer, for 4 minutes at 37° C. During this incubation, the anti-human BNP 201.3 acridinium labeled antibodies bound to the magnetic microparticles/monoclonal antibody 8.1/BNP complexes.

Upon completion of the 4 minute incubation, the magnetic microparticles/monoclonal antibody 8.1/human BNP/labeled monoclonal antibody 201.3 and monoclonal antibody 8.1/BNP complexes were again magnetically captured into a pellet. The recaptured pellet was then repeatedly washed with buffer (1 mL), repeated 4 times. The magnetically captured monoclonal antibody 8.1 coated magnetic microparticles, human BNP and labeled monoclonal antibody 201.3) and monoclonal antibody 8.1/BNP complex pellets were then released.

The acridinium label (Abbott Laboratories, Abbott Park, Code 61444) was then triggered to emit light. This was accomplished by adding a low pH (pH 1) buffer containing $H_2O_2$ (1.32%) (List 6E23-65, Abbott Laboratories, Abbott Park, Ill.). This was dispensed in the amount of (100 µL) into individual reaction vessels containing the microparticle complexes and then vortexed. This step released the acridinium labeled anti-human BNP (Abbott Laboratories, Abbott Park, Ill.) monoclonal antibodies 201.3 (Abbott Laboratories, Abbott Park, Ill.), bound to the human BNP captured by the microparticles.

The magnetic microparticles were then magnetically captured leaving the released acridinium labeled anti-BNP antibodies (monoclonal antibody 201.3) in the reaction mixture solution. This was followed by addition (300 µL) of a pH 13 buffer (Abbott Laboratories, Abbott Park, Ill.) which "triggers" light, relative light units (RLU), production from the acridinium that had been released into the solution. The amount of light that was generated was used to determine the quantity of human BNP detected in the sample.

Human proBNP Detection

Each sample dilution was dispensed in the amount of 100 µL into the individual reaction vessels. At the same time, 0.10% EDAC-coated magnetic microparticles (50 µL) ((Polymer Laboratories Ltd, now part of Varian, Inc., Shropshire, UK) coated with anti-human BNP/human proBNP monoclonal antibody 8.1 (Scios, Sunnyvale, Calif.; A.T.C.C. Accession No. HB-12056) were dispensed in the amount of 50 µL into the same reaction vessel. The reaction vessel was then vortexed to mix the sample and magnetic microparticles. Each reaction mixture was incubated for 18 minutes at 37° C.

During this incubation, any human proBNP in the samples was captured by monoclonal antibodies 8.1 that were coated onto the magnetic microparticles.

Upon completion of an 18 minute incubation, the monoclonal antibody 8.1 coated magnetic microparticles and monoclonal antibody 8.1/proBNP complexes were magnetically captured, and immobilized into a pellet on the side of the reaction vessel. The immobilized magnetic microparticles and monoclonal antibody 8.1/human proBNP complex pellet was then washed by alternately aspirating the liquid from the vessel, and then adding assay kit wash buffer (ARCHITECT® wash buffer, available from Abbott Laboratories, Abbott Park, Ill.) into the reaction vessel (1 mL wash buffer, repeated 4 times). This process removed any unbound human proBNP from the reaction mixture. The magnetically captured microparticle human proBNP monoclonal antibody 8.1/proBNP complexes formed during the 18 minute incubation remained in the reaction vessel. The magnetic microparticle monoclonal antibody 8.1/human proBNP complex pellet was then released from the magnet.

During a second incubation of 4 minutes, anti-human NT-proBNP/anti-human proBNP acridinium (Abbott Laboratories, Abbott Park) labeled monoclonal antibody 15C4 (HyTest, Turku, Finland; Catalog No. 4TN1) was dispensed in the amount of 50 µL into individual reaction vessels containing only monoclonal antibody 8.1 coated magnetic microparticles monoclonal antibody 8.1/human proBNP complexes. This reaction mixture was then vortexed to disperse the microparticle pellet.

The magnetic microparticles monoclonal antibody 8.1/proBNP complexes were incubated with acridinium (Abbott Laboratories, Abbott Park, Code 88333) labeled anti-human proBNP 15C4 monoclonal antibodies, in buffer, for 4 minutes at 37° C. During this incubation, the anti-human proBNP 15C4 acridinium labeled antibodies bound to the magnetic microparticles with monoclonal antibody 8.1/proBNP complexes.

Upon completion of the 4 minute incubation, the magnetic microparticle, monoclonal antibody 8.1/human proBNP/labeled monoclonal antibody 15C4 complexes were again magnetically captured into a pellet. The recaptured pellet was then repeatedly washed with buffer (1 mL), repeated 4 times. The magnetically captured monoclonal antibody 8.1 coated magnetic microparticles, human proBNP and labeled antibody monoclonal antibody 15C4 and monoclonal antibody 8.1/proBNP complex pellet was then released.

The acridinium label (Abbott Laboratories, Abbott Park) was then triggered to emit light. This was accomplished by adding a low pH (pH 1) buffer containing $H_2O_2$ (1.32%) (List 6E23-65, Abbott Laboratories, Abbott Park, Ill.). This was dispensed in the amount of (100 µL) into individual reaction cells containing the microparticle complexes and then vortexed. This step released the acridinium labeled anti-human proBNP (Abbott Laboratories, Abbott Park, Ill.) monoclonal antibodies 15C4, that had been bound to human proBNP captured by the microparticles.

The magnetic microparticles were then magnetically captured leaving the released acridinium labeled anti-proBNP antibodies (monoclonal antibody 15C4) in the reaction mixture solution. This was followed by addition (300 µL) of a pH 13 buffer (Abbott Laboratories, Abbott Park, Ill.) which "triggers" light, relative light units (RLU), production from the acridinium released into the solution. The amount of light that was generated was used to determine the quantity of human proBNP detected in the sample.

Human NT-proBNP Detection

Each sample dilution was dispensed in the amount of 100 µL into the individual reaction vessels. At the same time, 0.10% EDAC-coated magnetic microparticles (50 µL) (Polymer Laboratories Ltd, now part of Varian, Inc., Shropshire, UK) coated with anti-human NT pro BNP/anti-human proBNP monoclonal antibody 15F11 (HyTest, Turku, Finland; Catalog No. 4TN1) were dispensed in the amount of 50 µL into the same reaction vessel. The reaction vessel was then vortexed to mix the sample and magnetic microparticles. Each reaction mixture was incubated for 18 minutes at 37° C.

During this incubation, any human NT proBNP in the samples were captured by monoclonal antibodies 15F11 that were coated onto the magnetic microparticles.

Upon completion of an 18 minute incubation, the 15F11 coated magnetic microparticles and monoclonal antibody 15F11/NT-proBNP complexes were magnetically captured and immobilized into a pellet on the side of the reaction vessel. The immobilized magnetic microparticle and the monoclonal antibody 15F11/NT-proBNP complex pellet were then washed by alternately aspirating the liquid from the vessel, and then adding assay kit wash buffer (ARCHITECT® wash buffer, available from Abbott Laboratories, Abbott Park, Ill.) into the reaction vessel (1 mL wash buffer, repeated 4 times). This process removed any unbound human NT-proBNP from the reaction mixture. The magnetically captured coated magnetic microparticles human NT-proBNP monoclonal antibody 15F11/NT-proBNP complex pellet formed during the 18 minute incubation remained in the reaction vessel. The magnetic microparticle monoclonal antibody 15F11/human NT-proBNP complex pellet was then released from the magnet.

During the second incubation of 4 minutes, anti-human NT proBNP/anti-human proBNP acridinium (Abbott Laboratories, Abbott Park) labeled monoclonal antibody 15C4 (HyTest, Turku, Finland; Catalog No. 4TN1) was dispensed in the amount of 50 µL into individual reaction vessels containing only the 15F11 coated magnetic microparticles and monoclonal antibody 15F11/NT-proBNP complexes. This reaction mixture was then vortexed to disperse the microparticle pellet.

Upon completion of the 4 minute incubation, the magnetic microparticle monoclonal antibody 15F11/NT-proBNP/labeled monoclonal antibody 15C4 complexes were again magnetically captured into a pellet. The recaptured pellet was then repeatedly washed with buffer (1 mL), repeated 4 times. The magnetically captured coated magnetic microparticles, anti-human NT proBNP/anti-human proBNP labeled monoclonal antibody 15C4 and monoclonal antibody 15F11/human NT-proBNP complex pellet was then released from the magnet.

The acridinium label (Abbott Laboratories, Abbott Park) was then triggered to emit light. This was accomplished by adding a low pH (pH 1) buffer containing $H_2O_2$ (1.32%) (List 6E23-65, Abbott Laboratories, Abbott Park, Ill.). This was dispensed in the amount of (100 µL) to the individual reaction vessels containing the microparticle complexes and then vortexed. This step released the acridinium labeled anti-human NT-proBNP (Abbott Laboratories, Abbott Park, Ill.) monoclonal antibodies 15C4 (Abbott Laboratories, Abbott Park, Ill.), that had been bound to human NT-proBNP captured by the microparticles.

The magnetic microparticles were then magnetically captured leaving the released acridinium labeled NT-proBNP antibodies (monoclonal antibody 15C4) in the reaction mixture solution. This was followed by addition (300 µL) of a pH 13 buffer (Abbott Laboratories, Abbott Park, Ill.) which "triggers" light, relative light units (RLU), production from the acridinium released into the solution. The amount of light that was generated was used to determine the quantity of human NT-human proBNP detected in the sample.

The results are shown below in Table 1 and in FIG. 1A, FIG. 1B and FIG. 1C.

TABLE 1

| | | Capture Monoclonal Anitbody | | |
| | | 15F11 | 8.1 | 8.1 |
| | | Labeled Monoclonal Antibody | | |
| | | 15C4 | 15C4 | 201.3 |
| Sample | pM | mean rlus | mean rlus | mean rlus |
| BNP | 0 | 1195 | 745 | 212 |
| | 43.8 | 1038 | 567 | 11033 |
| | 86.6 | 1082 | 713 | 29955 |
| | 288.7 | 1127 | 732 | 257748 |
| | 577.4 | 1145 | 701 | 1029195 |
| proBNP | 0 | 1135 | 659 | 283 |
| | 43.8 | 1302 | 5478 | 276 |
| | 86.6 | 1488 | 12015 | 262 |
| | 288.7 | 2214 | 42997 | 255 |
| | 577.4 | 3591 | 116479 | 276 |

TABLE 1-continued

| | | Capture Monoclonal Anitbody | | |
| | | 15F11 | 8.1 | 8.1 |
| | | Labeled Monoclonal Antibody | | |
| | | 15C4 | 15C4 | 201.3 |
| Sample | pM | mean rlus | mean rlus | mean rlus |
| NT-proBNP | 0 | 1135 | 659 | 283 |
| | 43.8 | 22439 | 643 | 251 |
| | 86.6 | 62653 | 606 | 269 |
| | 288.7 | 316876 | 637 | 264 |
| | 577.4 | 657865 | 687 | 265 |

TABLE 2

| Kit Reagents | | Analyte Detection | | |
| | | Human | | |
| Capture Mab | Labeled Mab | Human BNP | proBNP | Human NT proBNP |
| 15F11 | 15C4 | − | − | + |
| 8.1 | 15C4 | − | + | − |
| 8.1 | 201.3 | + | − | − |

Discussion Of Results

A two step sandwich immunoassay was used to quantitate human NT proBNP, human proBNP and human BNP. The three analytes were detected using only two immunoassay kits. As used herein, what is meant by "immunoassay kit" is a kit composed of an analyte capture reagent (namely, magnetic microparticles coated with monoclonal antibody specific for the intended analyte) and a detection reagent (namely, a monoclonal antibody specific for the intended analyte, labeled with acridinium). A representation of two typical immunoassay kits is shown below in Table 3.

TABLE 3

| | Kit A | Kit B |
| Detection Reagent | A | B |
| Capture Reagent | A | B |
| Detected Analyte | A | B |

By using a capture reagent from one immunoassay kit (e.g., Kit A) and the detection reagent from another immunoassay kit (e.g., Kit B), a third analyte which shares epitopes A and B can be detected (AB). This representation is shown below in Table 4 (See, FIGS. 2A and 2B).

TABLE 4

| Kit Reagents | | | | |
| Detection | Capture | Analytes Detected | | |
| A | A | A | — | — |
| A | B | — | AB | — |
| B | B | — | — | B |

The present disclosure uses only two types of magnetic particles, each coated with different capture monoclonal antibodies, and only two different labeled monoclonal antibodies, to specifically detect three analytes, human BNP, human proBNP and human NT-proBNP.

Human BNP was detected by creating a "sandwich" using monoclonal antibodies specific for two separate BNP epitopes found on the human BNP.

Human NT-proBNP was detected by creating a "sandwich" using monoclonal antibodies specific for two separate human NT-proBNP epitopes found on the human NT-proBNP.

Human proBNP was detected using two monoclonal antibodies, one specific for a human BNP epitope and the other monoclonal antibody specific for a human NT proBNP epitope. Human proBNP contains epitopes that are found in the human BNP and human NT proBNP. A BNP capture monoclonal antibody formed a sandwich with a human proBNP labeled detection monoclonal antibody, permitting the detection of human proBNP.

Using the capture monoclonal antibody of one analyte, with the labeled detection antibody of a second analyte, is the basis for detection of three analytes (human BNP, human proBNP and human NT-proBNP) using only two kits.

One skilled in the art would readily appreciate that the present disclosure is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the disclosure. It will be readily apparent to one skilled in the art that varying substitutions and modifications may be made to the disclosure disclosed herein without departing from the scope and spirit of the disclosure.

All patents and publications mentioned in the specification are indicative of the levels of those skilled in the art to which the disclosure pertains. All patents and publications are herein incorporated by reference to the same extent as if each individual publication was specifically and individually indicated to be incorporated by reference.

The disclosure illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

What is claimed is:

1. An immunoassay method for quantifying the amount of human NT-pro B-type natriuretic peptide ("human NT-proBNP"), human pro B-type natriuretic peptide ("human proBNP") and human brain natriuretic peptide ("hBNP") in a test sample being tested for or suspected of containing human NT-proBNP, human proBNP and hBNP, the immunoassay method comprising the steps of:
(a) contacting a test sample with (i) a first capture antibody that binds to human NT-proBNP and that has been immobilized onto a solid phase to produce a first immobilized antibody and forming a first mixture comprising a first capture antibody-human NT-proBNP complex; (ii) a second capture antibody that binds to human proBNP and that has been immobilized onto a solid phase to produce a second immobilized antibody and forming a second mixture comprising a second capture antibody-human proBNP complex; and (iii) the second capture antibody, which in addition to binding to human proBNP also binds hBNP, and that has been immobilized onto a solid phase to produce a third immobilized antibody and forming a third mixture comprising a second capture antibody-hBNP complex, wherein said first capture antibody comprises antibody 151F11 and the second capture antibody comprises antibody 8.1;
(b) contacting said first mixture comprising the first capture antibody-human NT-proBNP complex with a first detection antibody which binds to human NT-proBNP and that has been conjugated to a first detectable label to form a fourth mixture comprising a first capture antibody-human NT-proBNP-first detection antibody complex, wherein the first detection antibody is 15C4;

(c) contacting the second mixture comprising the second capture antibody-human proBNP complex with the first detection antibody which, in addition to binding to human NT-proBNP, also binds to human proBNP, and that has been conjugated to the first detectable label to form a fifth mixture comprising a second capture antibody-human proBNP-first detection antibody complex, wherein the first detection antibody is antibody 15C4;

(d) contacting the third mixture comprising the second capture antibody-hBNP complex with a second detection antibody which binds hBNP and that has been conjugated to a second detectable label to form a sixth mixture comprising a second capture antibody-hBNP-second detection antibody complex, wherein the second detection antibody is antibody 201.3; and (e) determining the amount of (i) first capture antibody-human NT-proBNP-first detection antibody complex formed in step (b) by detecting the first detectable label as a measure of the amount of human NT-proBNP contained in the test sample; (ii) the second capture antibody-human proBNP-first detection antibody complex formed in step (c) by detecting the first detectable label as a measure of the amount of human proBNP contained in the test sample; and (iii) the second capture antibody-hBNP-second detection antibody complex formed in step (d) by detecting the second detectable label as a measure of the amount of hBNP contained in the test sample.

2. The immunoassay method of claim 1, wherein the solid phase is selected from the group consisting of a magnetic particle, bead, test tube, microtiter plate, cuvette, membrane, a scaffolding molecule, film, filter paper, disc, and chip.

3. The immunoassay method of claim 1, wherein the first detectable label of the first detection antibody is selected from the group consisting of a radioactive label, an enzymatic label, a chemiluminescent label, a fluorescent label, a thermometric label, and an immuno-polymerase chain reaction label.

4. The immunoassay method of claim 1, wherein the second detectable label of the second detection antibody is selected from the group consisting of a radioactive label, an enzymatic label, a chemiluminescent label, a fluorescent label, a thermometric label, and an immuno-polymerase chain reaction label.

5. An immunoassay method for quantifying the amount of human NT-pro B-type natriuretic peptide ("human NT-proBNP"), human pro B-type natriuretic peptide ("human proBNP") and human brain natriuretic peptide ("hBNP") in a test sample being tested for or suspected of containing human NT-proBNP, human proBNP and hBNP, the immunoassay method comprising the steps of:

(a) contacting a test sample with (i) a first detection antibody which binds to human NT-proBNP and that has been conjugated to a first detectable label to form a first mixture comprising a human NT-proBNP-first detection antibody complex; (ii) the first detection antibody, which in addition to binding to human NT-proBNP also binds to human proBNP, and that has been conjugated to the first detectable label to form a second mixture comprising a human proBNP-first detection complex; and (iii) a second detection antibody which binds to hBNP and that has been conjugated to a second detectable label to further form a third mixture comprising a hBNP-second detection antibody complex, wherein the first detection antibody is antibody 15C4 and the second detection antibody is antibody 201.3;

(b) contacting said first mixture comprising the human NT-proBNP- first detection antibody complex with a first capture antibody that binds to human NT-proBNP and that has been immobilized onto a solid phase to produce a first immobilized antibody to form a fourth mixture comprising a first capture antibody-human NT-proBNP-first detection antibody complex, wherein the first capture antibody is 15F11;

(c) contacting said second mixture comprising the human proBNP- first detection antibody complex with a second capture antibody that binds to human proBNP and that has been immobilized onto a solid phase to produce a second immobilized antibody to form a fifth mixture comprising a second capture antibody-human proBNP-first detection antibody complex, wherein the second capture antibody is 8.1;

(d) contacting the third mixture comprising the hBNP-second detection antibody complex with the second capture antibody, which in addition to binding to human proBNP also binds to hBNP, and that has been immobilized onto a solid phase to produce a second immobilized antibody to form a sixth mixture comprising a second capture antibody-human BNP-second detection antibody complex, wherein the second capture antibody is 8.1; and (e) determining the amount of (i) first capture antibody-human NT-proBNP-first detection antibody complex formed in step (b) by detecting the first detectable label as a measure of the amount of human NT-proBNP contained in the test sample; (ii) the second capture antibody-human proBNP-first detection antibody complex formed in step (c) by detecting the first detectable label as a measure of the amount of human proBNP contained in the test sample; and (iii) the second capture antibody-hBNP-second detection antibody complex formed in step (d) by detecting the second detectable label as a measure of the amount of hBNP contained in the test sample.

6. The immunoassay method of claim 5, wherein the solid phase is selected from the group consisting of a magnetic particle, bead, test tube, microtiter plate, cuvette, membrane, a scaffolding molecule, film, filter paper, disc, and chip.

7. The immunoassay method of claim 5, wherein the first detectable label of the first detection antibody is selected from the group consisting of a radioactive label, an enzymatic label, a chemiluminescent label, a fluorescent label, a thermometric label, and an immuno-polymerase chain reaction label.

8. The immunoassay method of claim 5, wherein the second detectable label of the second detection antibody is selected from the group consisting of a radioactive label, an enzymatic label, a chemiluminescent label, a fluorescent label, a thermometric label, and an immuno-polymerase chain reaction label.

* * * * *

SEQUENCE LISTING

```
<160> NUMBER OF SEQ ID NOS: 4

<210> SEQ ID NO 1
<211> LENGTH: 134
<212> TYPE: PRT
<213> ORGANISM: Homo sapiens

<400> SEQUENCE: 1

Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
                20                  25                  30

Gly Ser Ala Ser Asp Leu Glu Thr Ser Gly Leu Gln Glu Gln Arg Asn
            35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
            100                 105                 110

Phe Gly Arg Lys Met Asp Arg Ile Ser Ser Ser Ser Gly Leu Gly Cys
        115                 120                 125

Lys Val Leu Arg Arg His
    130

<210> SEQ ID NO 2
<211> LENGTH: 108
<212> TYPE: PRT
<213> ORGANISM: Homo sapiens

<400> SEQUENCE: 2
```

```
His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
            35                  40                  45

Gly Val Trp Lys Ser Arg Glu Val Ala Thr Glu Gly Ile Arg Gly His
            50                  55                  60

Arg Lys Met Val Leu Tyr Thr Leu Arg Ala Pro Arg Ser Pro Lys Met
65                  70                  75                  80

Val Gln Gly Ser Gly Cys Phe Gly Arg Lys Met Asp Arg Ile Ser Ser
                85                  90                  95

Ser Ser Gly Leu Gly Cys Lys Val Leu Arg Arg His
            100                 105

<210> SEQ ID NO 3
<211> LENGTH: 76
<212> TYPE: PRT
<213> ORGANISM: Homo sapiens

<400> SEQUENCE: 3

Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
            20                  25                  30

Gly Ser Ala Ser Asp Leu Glu Thr Ser Gly Leu Gln Glu Gln Arg Asn
            35                  40                  45

His Leu Gln Gly Lys Leu Ser Glu Leu Gln Val Glu Gln Thr Ser Leu
        50                  55                  60

Glu Pro Leu Gln Glu Ser Pro Arg Pro Thr Gly Val
65                  70                  75

<210> SEQ ID NO 4
<211> LENGTH: 32
<212> TYPE: PRT
<213> ORGANISM: Homo sapiens

<400> SEQUENCE: 4

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30
```